United States Patent [19]

Munk

[11] 4,032,445
[45] June 28, 1977

[54] LIQUID CHROMATOGRAPHY PUMPING SYSTEM WITH COMPENSATION MEANS FOR LIQUID COMPRESSIBILITY

[75] Inventor: Miner N. Munk, Walnut Creek, Calif.

[73] Assignee: Varian Associates, Palo Alto, Calif.

[22] Filed: Nov. 10, 1975

[21] Appl. No.: 630,400

[52] U.S. Cl. .............................. 210/103; 210/137; 210/198 C
[51] Int. Cl.² ...................................... B01D 15/08
[58] Field of Search ................ 210/31 C, 101, 136, 210/137, 198 C, 103; 73/61.1 C; 55/386, 197

[56] References Cited

UNITED STATES PATENTS

| 2,036,489 | 4/1936 | Murphy | 210/137 X |
| 2,143,229 | 1/1939 | Russel | 210/137 |
| 3,446,057 | 5/1969 | Bakalyar et al. | 210/31 C |
| 3,670,890 | 6/1972 | Hall et al. | 210/137 X |
| 3,779,384 | 12/1973 | Stahlkopf | 210/137 X |
| 3,917,531 | 11/1975 | Magnussen | 210/198 C |

OTHER PUBLICATIONS

Introduction to Modern Liquid Chromatography by Spraer et al. John Wiler & Sons, New York, pp. 94, 97, and 99–102 relied on, 1974.

*Primary Examiner*—John Adee
*Attorney, Agent, or Firm*—Stanley Z. Cole; Gerald M. Fisher; John J. Morrissey

[57] ABSTRACT

In a liquid chromatography system including a chromatographic column, a reservoir for a slightly compressible liquid mobile phase, piston means cooperating with the reservoir for pumping the liquid phase through the chromatographic column, and means for displacing the piston at a pre-selected velocity, an improvement is disclosed enabling maintenance of a constant flow in the presence of flow resistance changes at the chromatographic column. Such flow resistance changes may arise, for example, in consequence of viscosity changes occurring in the liquid phase during the course of gradient elution operation. According to the improvement, pressure control means are provided in the flow path between the reservoir and column, the pressure control means being adapted for maintaining a substantially constant pressure at the reservoir. In consequence, flow rate changes arising from expansion or contraction of the liquid phase in consequence of compressibility are precluded.

6 Claims, 3 Drawing Figures

LIQUID CHROMATOGRAPHY PUMPING SYSTEM WITH COMPENSATION MEANS FOR LIQUID COMPRESSIBILITY

BACKGROUND OF INVENTION

This invention relates generally to chromatography systems, and more specifically relates to liquid chromatography systems.

Chromatography is a separation method wherein a mixture of components (called the "sample" or "sample mixture") is placed as a zone at one end of a system containing a stationery phase and a mobile phase. Each component of the sample distributes itself in dynamic equilibrium between the two phases, in a ratio characteristic of that component. As a result, the flowing mobile phase causes each individual component zone to migrate at a characteristic rate, and the zones become separated after a period of time. There are various types of chromatography, e.g., liquid chromatography, gas chromatography, thin-layer chromatography, etc. The major difference between these various chromatographic methods is the physical state of the mobile phase (gas or liquid) and the manner in which the stationary phase is supported (e.g., coated on an inert granular material packed in a tube, coated on an inert plate, etc.). In each method, the separation mechanism is essentially the same, i.e., distribution of the sample components between the mobile phase and a stationary phase. When the method is used for chemical analysis, a detector is often placed at the other end of the system, so as to monitor the passage of the component zones as they emerge from the system. The signal from the detector is displayed on a recording device such as a strip chart recorder, and the record indicates both qualitative and quantitative information regarding the components of the sample.

It is often desirable for a chromatographic system to provide high resolution (i.e., a large degree of component separation with narrow zones), evenly spaced component zones, rapid separation, and a satisfactory record from a very small sample. The behavior of the system described in these terms may be called the "performance" of the system. It is well-known in the chromatography art to improve system performance by changing one of the following system variables during the course of the analysis: temperature, chemical composition of the mobile phase, and flow rate of the mobile phase. For example, in gas chromatography the temperature of the system is often varied as a pre-selected function of time. This technique is known as "temperature programming", and it improves the performance of the system, especially with samples containing components which boil over a wide temperature range.

Analagous to temperature programming in gas chromatography is the use of "gradient elution" in liquid chromatography. Gradient elution refers to changing the chemical composition of the mobile phase (also called the "eluent" or "eluting solvent") as a function of time, thereby improving the performance of the system, especially with samples containing components which vary widely in chemical properties. A further example of changing the chromatographic variables is the recent development of "flow programming" in gas and liquid chromatography, wherein the flow rate of the mobile phase is changed as a pre-selected function of time. As mentioned previously, the object of changing or "programming" the individual chromatographic system variables during the analysis is to improve one or more aspects of system performance. Further discussion with regard to gradient elution techniques and the factors affecting system performance may be found in various places in the art, including, e.g., U.S. Pat. No. 3,446,057, and the publication by L. R. Snyder appearing in Chromatography Review 7, 1 (1965).

The normal and usual arrangement in chromatography apparatus of the type considered herein entails use of one or more reservoirs, which are basically in the nature of syringe pumps. A given said reservoir thus may comprise a cylindrical tube or the like, having a volume V. A piston of circular cross-section is mounted for axially-directed movement in the cylinder, and is normally driven by motor means at a pre-selected velocity which may be constant over a given period of time, or which varies in accordance with the gradient elution program.

It has been found that a most serious technical problem arising in the use of apparatus as mentioned above derives from a failure to account for compressibility of the several solvents. In particular, during the course of gradient elution work, viscosity changes occur in the composite liquid phase flowing through the chromatography column. This, in turn, induces pressure changes at the input of the said column, i.e., in the flow path between the reservoirs and the said column. By virtue of the compressibility of the various solvents, these pressure changes, interacting with the already programmed velocities of the pistons, induce density changes in the solvents, which is to say, changes in the volume of a given mass of the said solvents. The net effect of these changes, which, of course, arise by virtue of compressibility of the solvents, is to effectively change the flow rates of one or more of the solvents — with possibly highly detrimental effects on system performance.

The phenomenon in turn, under such conditions, may be further appreciated by considering that the pressure drop across the chromatographic column is represented by the simple expression:

$$P = \dot{V}R \qquad (1)$$

where P is the pressure drop or pressure in the pump, $\dot{V}$ is the volumetric flow rate, and R is the column resistance in appropriate units. The resistance R is proportional to viscosity for laminar flow — which normally prevails in liquid chromatography. As the viscosity changes, so does the column resistance. Since the pump is pre-programmed to have a certain piston velocity movement, which over a given time period maintains a constant volumetric flow rate, the pressure in the pump increases with increase in viscosity of the fluid. This increase in pressure causes compression of the liquid in the pump (or pumps in the gradient system). This compression subtracts from the output flow rate of the pump, so that the flow rate is no longer constant. This effect can be dramatic when the pump reservoirs are nearly full, and the change in solvent composition is rapid compared to the output flow rate of the pumping system. Thus it may readily be shown that in a gradient system based on water and methanol, wherein the gradient operation is such as to proceed from water to 40% methanol in water over a period of 10 minutes, and wherein the pressure with water is 2500 psi, the nominal flow rate is 60 ml/hr, and the volume of each reservoir is 200 cc, a 40% deviation of actual flow from the nominally set flow rate can ensue.

One conceivable solution to the foregoing difficulty is to provide each pump in the gradient system with a flow rate measuring device, and feed back the response from such device to maintain a constant or other prescribed flow rate function from the pump. The complexity of each arrangement however introduces inordinate cost and complexity into a pumping system.

In accordance with the foregoing, it may be regarded as an object of the present invention, to provide means enabling maintenance of a constant flow in a liquid chromatography system in the presence of flow resistance changes at the chromatographic column of such system, which changes are induced by viscosity changes in the liquid phase deriving from gradient elution techniques. Changes in viscosity of lesser magnitude can arise from temperature variations. Column resistance can also change with change in column bed structure such as the phenomena usually referred to as bed settling.

It is a further object of the present invention to provide means enabling constant flow through the chromatographic column in a liquid chromatography system of the type considered in the preceding paragraph, wherein, further, the said means is of great simplicity thereby assuring ease of operation and low cost for construction thereof.

SUMMARY OF INVENTION

Now in accordance with the present invention, an improvement is provided which enables maintenance of a constant flow in the presence of flow resistance changes in the chromatographic column of a liquid chromatography system. The said system is of the general type which includes a chromatographic column, a reservoir for a slightly compressible liquid mobile phase, positive displacement piston pumping means cooperating with the reservoir as to enable pumping of the liquid phase through the chromatographic column, and means for displacing the piston at a pre-selected velocity. In accordance with the invention, pressure control means are provided in the flow path between the reservoir and the chromatographic column, the said means being adapted for maintaining a substantially constant pressure at the reservoir, to thereby preclude flow rate changes arising from expansion or contraction of the liquid phase in consequence of compressibility thereof. The invention is particularly applicable to a gradient elution type of system wherein a plurality of reservoirs and pumping means are incorporated. In this type of system, the pressure changes previously mentioned are a consequence of viscosity variations in the composite mobile phase passing into the chromatographic column, i.e., effectively the resistance offered by such column varies in accordance with the composition of the composite phase. These variations cause the pressure changes at the system reservoir in this type of system.

The pressure control means of the invention basically comprises an adjustable flow resistance, and can take the form of a manually adjustable back pressure regulating valve. In a preferable form of the invention, however, a pressure detection means is provided in the flow path at the pump outlet, and a servo means responsive to the detected pressure adjusts a downstream of the flow resistance to maintain the aforementioned constant pressure.

BRIEF DESCRIPTION OF DRAWINGS

The invention is diagrammatically illustrated, by way of example, in the drawings appended hereto, in which.

DESCRIPTION OF PREFERRED EMBODIMENT

Figure 1:
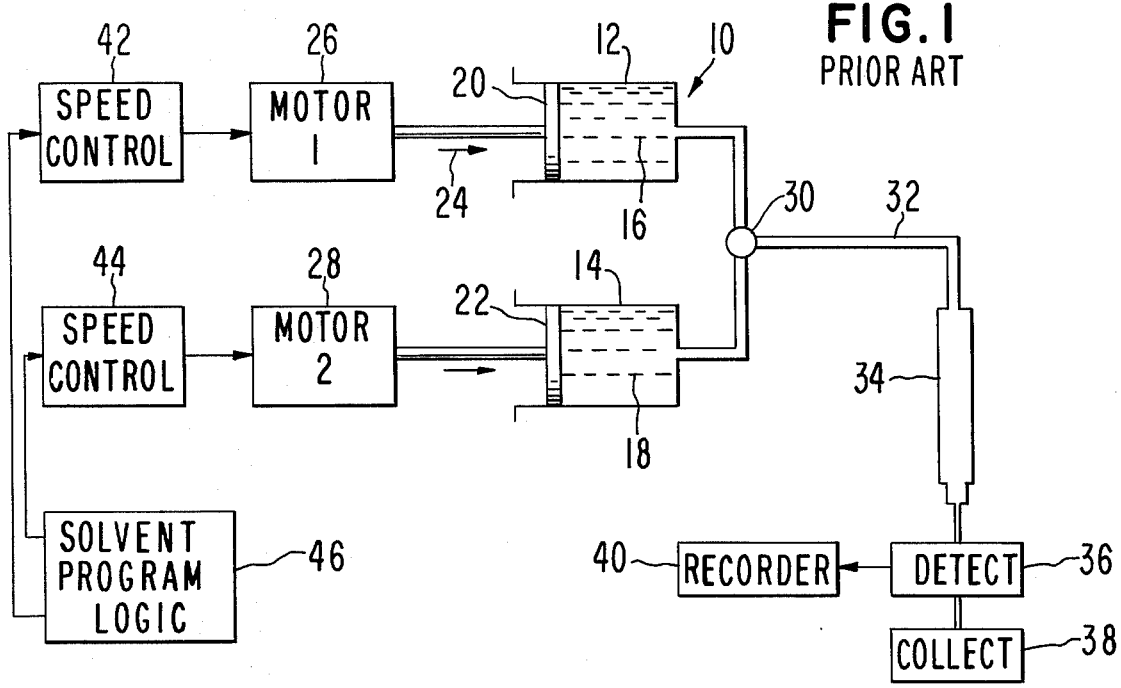
FIG. 1 is a highly schematic depiction of prior art chromatography apparatus of the type to which the present invention is particularly applicable.

In order to gain a full appreciation of the present invention and its mode of operation reference may initially be had to FIG. 1 herein, which sets forth in highly schematic fashion a prior art chromatography system 10 of the type to which the present invention is particularly applicable. The principles of the system depicted in this FIG. 1 are in general very well-known to those familiar with the present art, and hence details of the system are not set forth in any great mechanical detail.

The system 10 is of the type intended for operation in a so-called gradient elution mode. The objectives and general mode of practice of this type of system have been set forth in the Background portion of this specification. The system 10 thus includes first and second reservoirs 12 and 14, which may contain distinctly different solvents 16 and 18 as, for example, methanol and water, respectively. The reservoirs may be considered for present purposes as being of generally circular cross-section, i.e., each reservoir is cylindrical in form. Pistons 20 and 22 engage with the internal walls of reservoirs 12 and 14, and are positively displaced in the direction 24 by first and second motor means 26 and 28, in order to enable a positive displacement pumping action from the said reservoirs. The two liquid solvents 16 and 18 thus enter a mixing junction 30, and thereupon the composite liquid phase passes through a conduit 32, and thence proceeds to a liquid chromatography column 34. Again, as is well-known in the present art, the output from column 34 may be provided to a detector 36, and thence to a collector 38. The detector 36 may be associated with a suitable recorder 40.

Assuming, as will be useful for present purposes, that the system 10 is intended for operation in the aforementioned gradient elution mode, first and second speed controls 42 and 44 are provided for controlling the motors 26 and 28, respectively and thus the displacement velocities of the pistons 20 and 22, respectively. The speed controls 42 and 44 are regulated by means of the solvent program logic 46 in accordance with a pre-selected program, i.e., the respective advance rates of the pistons 20 and 22 are regulated so as to provide a desired ratio between solvents 16 and 18 as a function of time. At the same time, as is the usual objective in the present type of system, the total flow proceeding through the mixing junction 30 into conduit 32 is intended to be held at a constant value, so that volumetric flow through the column 34 is maintained at a constant.

The problem to which the present invention addresses itself hs been touched upon in the "Background" portion of this specification. In particular, and continuing to refer to FIG. 1, if it is assumed that reservoir 12 has a volume V and reservoir 14 the same volume V, then the incremental mass change dm occurring in each cylinder for an incremental change in volume of the cylinder, i.e., occuring in consequence of piston advance, is given by the expression $$dm = \rho dv + v d\rho \tag{2}$$

where $\approx dm/dv$ is defined as the density of the solvent in the reservoir being considered.

Thus, the incremental mass change occurring in the reservoir 12 is given by the equation $$\dot{m}_1 = dm_1/dt = (\rho \, dV_1/dt) + (V \, d\rho_1/dt).$$

The compressibility $\beta$ of a given solvent in the reservoir can be expressed by the identity $$\beta - 1/V \, (dV/dP),$$

where P is the pressure of the solvent. Substituting $dV = 1/\rho \, dm$ yields the equation $$- 1/V \, (dv/dP) = 1/\rho \, (d\rho/dP).$$

Thus, the incremental mass change with respect to time occurring in the reservoir 12 is expressed by the equation:

$$\dot{m}_1 = \rho_1 \dot{V}_1 - \rho_1 \beta_1 V_1 \, (d\rho/dt) \tag{3}$$

Similarly, the incremental mass change with respect to time occurring in the reservoir 14 is expressed by the equation:

$$\dot{m}_2 = \rho_2 \dot{V}_2 - \rho_2 \beta_2 (V_2 \, (dP/dt) \tag{4}$$

The flow rate V of a given volume V of the composite fluid phase passing through the mixing junction 30 into the conduit 32 can be expressed in terms of the incremental mass changes with respect to time occurring in the reservoirs 12 and 14 by the equation $V = 1/\rho_{eff} (m_1 + m_2)$, where $\rho_{eff}$ defines the effective density of the composite fluid phase. Substituting for $m_1$ and $m_2$ from the equations (3) and (4):

$$\dot{V} = 1/\rho_{eff} \, (\dot{m}_1 + \dot{m}_2) = 1/\rho_{eff} \, (\rho_1 \dot{V}_1 + \rho_2 \dot{V}_2) - 1/\rho_{eff} \, (\rho_1 \beta_1 V_1 + \rho_2 \beta_2 V_2) \, dP/dt \tag{5}$$

The first term on the right side of equation (5) is the actual flow rate if the solvents are both incompressible, i.e., if $\beta = \beta_2 = 0$. Thus, the flow rate of the composite fluid phase can be expressed as the sum of the nominal flow rate $\dot{V}_o$ and the perturbation $\dot{V}'$ on the nominal flow rate caused by compressibility of the solvents. Expressed as an equation, $\dot{V} = \dot{V}_o + \dot{V}'$. The nominal flow rate is given by:

$$\dot{V}_o = 1/\rho_{eff} (\rho_1 \dot{V}_1 + \rho_2 \dot{V}_2).$$

The change from the nominal flow rate due to compressibility is given by:

$$\dot{V}' = -1/\rho_{eff}(\rho_1\beta_1V_1 + \rho_2\beta_2V_2) \, dP/dt \tag{6}$$

Since $\rho_{eff}$ is intermediate in value between $\rho_1$ and $\rho_2$, and since liquid densities for representative fluids employed in liquid chromatography have values of $\rho$ roughly between 0.6 and 1.0, a simplifying approximation is warranted, i.e., that $$\rho_1 \approx \rho_{eff} \approx \rho_2 \tag{7}$$

Based upon said approximation it follows that $$\dot{V}' \approx - (\beta_1 V_1 + \beta_2 V_2) \, dP/dt. \tag{8}$$

The equation (8) above, when applied to the situation previously mentioned, i.e., where solvent 16 is water and solvent 18 is methanol, and where the program instituted by the logic 46 causes the composition of the fluid phase passing into the conduit 32 to change linearly in 10 minutes from 100% water to a composite of 60% water and 40% methanol indicates a surprisingly high error rate. By way of illustration, the pressure of the water in reservoir 12 may be assumed to be 2500 psi with a nominal flow rate of 60 ml/hr through the conduit 32. It may further be assumed that water is incompressible. A typical volume for the reservoir 12 is 200 ml. The viscosity of a composite fluid phase comprising 60% water and 40% methanol is approximately twice the viscosity of 100% water; and consequently in order to maintain the same flow rate of 60 ml/hr through the conduit 32 as was provided initially for 100% water, it is necessary that the pressure drop for the composite 60% water and 40% methanol phase in the conduit 32 be two times that for 100% water. It follows that $$\frac{dP}{dt} = \frac{(5000 - 2500) \text{ psi}/15 \text{ psi/atm}}{10 \text{ min}/60 \text{ min/hr}} = 1000 \text{ atm/hr}.$$

In the present example $\beta_1 = 40 \times 10^{-6}/\text{atm}$ and $\beta_2 = 80 \times 10^{-6}/\text{atm}$.
This provides $$(\beta_1 V_1 + \beta_2 V_2) \, dP/dt = 0.24 \times 1000 = 24 \text{ ml/hr}.$$

Thus, $\dot{V}' \approx -24$ ml/hr, which gives a 40% difference between the actual flow rate $\dot{V}$ and the nominal flow rate $\dot{V}_o$. This change from the nominal flow rate due to compressibility of the composite fluid phase, in the example illustrated, can result in a very large change from the nominal separation time experienced by the composite fluid phase in the chromatographic column. Since the identification of components in liquid chromatography is based upon the time of elution, a variation of the actual flow rate from the nominal flow rate of the fluid phase through the chromatographic column can lead to gross errors in qualitative analysis. The zone spread, i.e., the width of the peak of a specific elutant in the chromatogram, is a measure of column efficiency, and is a function of the flow rate. For the example considered, the diminution in flow rate results in wide, excessively broad peaks. Thus, when the chromatographic peaks are measured and analyzed to determine the amount of elutants, significant errors can occur in the quantitative determination because of the difference between the actual and the indicated flow rates.

Figure 2:
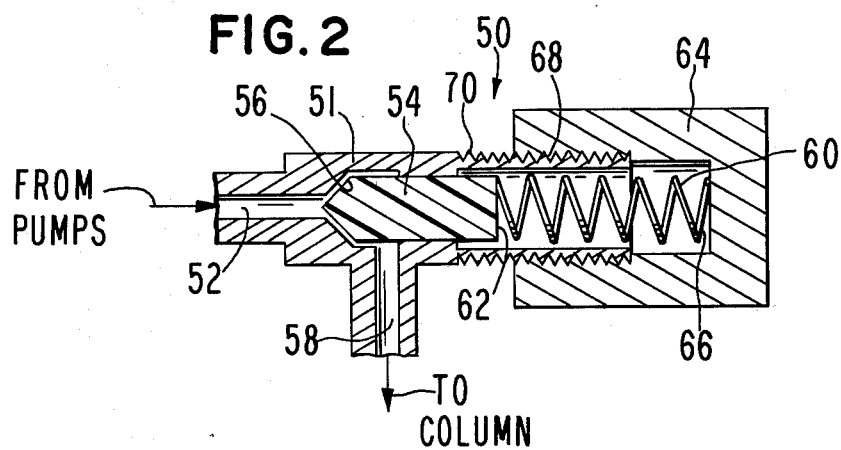
FIG. 2 is a schematic cross-sectional view of a manually operable back pressure regulating valve positioned at a portion of the FIG. 1 system, in accordance with the principles of the present invention.

In FIG. 2 herein, a manually operated back pressure regulating value means 50 is incorporated into the system of FIG. 1, so as to eliminate the aforementioned difficulties. The valve structure shown in FIG. 2 may be regarded as positioned in the conduit 32. For purposes of simplification, the remainder of the FIG. 1 system is not repeated in the FIG. 2 depiction, which is enlarged with respect to the schematically shown valve. The combined flow from the two reservoirs 12 and 14, i.e., the flow from junction 30, proceeds through channel 52 wherein it impinges against a regulatable flow restriction provided by means of the valve needle 54, which is seatable in a valve seat 56 defined in valve body 51. The flow outward from the valve arrangement 50 is via the passageway 58 toward chromatographic column 34. The valve needle 54 is loaded by means of a spring member 60, which bears against the rearward side 62 thereof. The needle pressure at which the valve opens is manually-regulatable by mens of cap 64. Thus, the distal end 66 of the spring 60 bears against the interior of the cap 64 and the cap's axial position may be adjusted by rotating same, since the internal threaded portion 68 thereof engages with a corresponding threaded portion 70 of valve body 51.

In use, the valve 50 is manually set to the maximum pressure anticipated during a run with specific solvents in the program.

Figure 3:
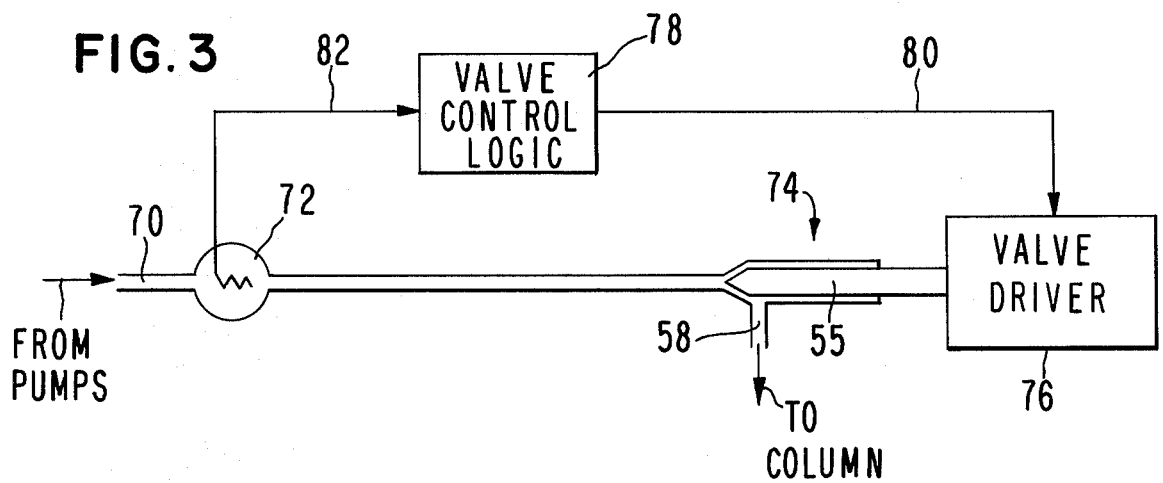
FIG. 3 illustrates the manner in which the FIG. 1 system may be modified by inclusion of an automatically regulated metering valve in accordance with the principles of the present invention.

The schematic arrangement of FIG. 3 represents a preferred version of the present invention. The basic mode of operation and connections of the embodiment shown in FIG. 3 are similar to those that have been discussed in connection with FIG. 2. Thus, the system of FIG. 3 may once again be regarded as installed in a portion of the FIG. 1 system wherein the composite flow from the plurality of reservoirs passes to the chromatographic column 34. Thus, as previously indicated, the arrangement of FIG. 3 can be regarded as inserted in conduit 32.

Thus, the flow from reservoirs 12 and 14 proceeds through the conduit 70. A pressure sensing transducer 72 is directly connected to sense the pressure in this conduit. The transducer 72 may comprise, for example, a strain gauge operating on piezoelectric principles; however, other types of sensitive pressure gauges may similarly be utilized, which yield outputs in an electrical form suitable for further manipulation.

A valve 74, which is of the metering type, is positioned downstream of the pressure sensing means 72.

In the present instance, instead of a manual control, which acts through spring-biasing means, a simple servo loop is utilized. In particular, opening and closing of valve 74, which essentially functions in the nature of a relief valve to maintain the constant pressure, is effected through valve driver means 76, which may constitute a simple solenoid or other device which acts to axially displace the valve needle 55. The axial position of the valve needle 55 similarly can vary over a continuous range in order to enable sensitive control. In either event, the control signal for causing the opening or closing of the valve 74 proceeds from valve control logic 78, via control line 80, to the valve driver means 76 the valve control logic 78 receiving its input signal via line 82 from the pressure sensing means 72. Thus, the pressure sensing means 72 may be set so that an error signal can proceed via line 80 to valve driver means 76 upon departure of system pressure from a preselected level. Driver means 76 then acts to vary the position of the valve needle 55 so as to restore the system pressure to its normal, pre-selected level. Thus, by such arrangement, compensation is automatically provided for variation in system pressure — which could otherwise occur by virtue of the resistance changes developed at column 34 in consequence of viscosity changes in the mobile phase passing through such column or other causes. In effect, a constant resistance is thus "seen" by the mobile phase flowing to the chromatographic column, in consequence of which the effect of the compressibility of the solvents may thereafter be substantially nullified.

While the present invention has been particularly set forth in terms of specific embodiments thereof, it will be understood in view of the present disclosure that numerous variations upon the invention are now enabled to those skilled in the art, which variations yet reside within the scope of the present invention.

Thus, for example, while the present invention has been particularly described with reference to its applicability to a chromatographic system employing a pair of reservoirs and wherein such system is utilized in a gradient elution mode of operation, it will be understood that more generally a plurality of the reservoirs may be utilized in a system of the type considered so that, in the type of system 10 of FIG. 1, any reasonable number of such reservoirs may simultaneously feed the junction 30 of the system. Similarly, the principles of the invention are applicable to a system including but a single reservoir.

Accordingly, the invention is to be brodly construed and limited only by the scope and spirit of the claims now appended hereto.

I claim:

1. In a liquid chromatography system of the type including a chromatographic column, a reservoir for a slightly compressible liquid mobile phase, positive displacement pumping means cooperating with said reservoir for pumping said liquid phase from said reservoir along a flow path to and through said chromatographic column, and means for driving said pumping means at a pre-selected velocity; the improvement, which enables maintenance of a constant flow through said column in the presence of a flow resistance change in said column, comprising:

pressure control means in the flow path between said reservoir and said column, said pressure control means comprising means for providing an adjustable flow resistance in said flow path, means for detecting the pressure in said flow path, and means responsive to the pressure detected by said pressure detecting means for adjusting the value of said flow resistance so as to maintain a substantially constant pressure at said reservoir, whereby to preclude flow rate changes that would otherwise arise from expansion or contraction of said liquid phase in consequence of the compressibility thereof.

2. A system in accordance with claim 1, including at least first and second reservoirs for first and second liquid phases, respectively; a common flow path connecting said first and second reservoirs to said chromatographic column; first and second positive displacement pumping means for pumping said first and second liquid phases, respectively, to said common flow path; said pressure control means being disposed along said common flow path.

3. A system in accordance with claim 2, further including programmable means for varying the respective displacement velocities of said first and second pumping means to enable a gradient elution mode of operation in said system, a change in viscosity for the composite of said first and second liquid phases flowing through said column effecting said flow resistance change in said column.

4. A system in accordance with claim 1, wherein said positive displacement pumping means comprises piston means, said piston being reciprocatable within said reservoir.

5. A system in accordance with claim 2, wherein each of said first and second positive displacement pumping means comprises a piston, said pistons being reciprocatable respectively in said first and second reservoirs.

6. A system in accordance with claim 3, wherein each of said first and second positive displacement pumping means comprises a piston, said pistons being reciprocatable respectively in said first and second reservoirs; and wherein said programmable means is capable of varying the displacement velocities of said pistons.

* * * * *